(12) United States Patent
Morgan et al.

(10) Patent No.: US 6,238,904 B1
(45) Date of Patent: May 29, 2001

(54) **TYPE II RESTRICTION ENDONUCLEASE, *HPY*CH4III, OBTAINABLE FROM *HELICOBACTER PYLORI* CH4 AND A PROCESS FOR PRODUCING THE SAME**

(75) Inventors: Richard D. Morgan, Middleton, MA (US); Qing Xu, Nashville, TN (US)

(73) Assignees: New England Biolabs, Inc., Beverly, MA (US); Vanderbilt University, Nashville, TN (US)

( * ) Notice: Subject to any disclaimer, the term of this patent is extended or adjusted under 35 U.S.C. 154(b) by 0 days.

(21) Appl. No.: 09/401,870

(22) Filed: Sep. 23, 1999

(51) Int. Cl.$^7$ .................................................. C12N 9/22
(52) U.S. Cl. ................................................ 435/199
(58) Field of Search .................................. 435/199

(56) References Cited

U.S. PATENT DOCUMENTS

| | | | |
|---|---|---|---|
| 5,179,015 | 1/1993 | Wilson et al. | 435/172.3 |
| 5,200,333 | 4/1993 | Wilson | 435/172.3 |

OTHER PUBLICATIONS

Lunnen, et al., Gene 74:25–32 (1988).
Piekarowicz, et al., Nucleic Acids Res. 19:1831–1835 (1991).
Endow, et al., J. Mol. Biol. 112:521 (1977).
Waalwijk, et al., Nucleic Acids Res., 5:3231 (1978).
Gingeras, et al., Proc. Natl. Acad. Sci., 80:402 (1983).
Gingeras, et al., Nucleic Acids Res. 5:4105 (1978).
Sanger, et al., Proc. Natl. Acad. Sci., 74:5463 (1977).
Brown, et al., J. Mol. 140:143 (1980).
Brooks, et al., Nucleic Acids Res. 17:979 (1989).

*Primary Examiner*—Charles E. Patterson, Jr.
(74) *Attorney, Agent, or Firm*—Gregory D. Williams

(57) ABSTRACT

In accordance with the present invention, there is provided a novel restriction endonuclease and its DNA obtainable from *Helicobacter pylori* CH4 (NEB#1236), hereinafter referred to as "*Hpy*CH4III", which endonuclease:

(1) recognizes the nucleotide sequence 5'-ACNGT-3' in a double-stranded DNA molecule as shown below,
 5'-ACN↓GT-3'
 3'-TG↑NCA-5'
 (wherein G represents guanine, C represents cytosine, A represents adenine, T represents thymine and N represents either G, C, A, or T);

(2) cleaves said sequence in the phosphodiester bonds between the N and G as indicated with the arrows; and (3) cleaves double-stranded PhiX174 DNA to produce 15 fragments, including fragments of 1284, 814, 536, 517, 454, 404, 302, 292, 270 and 222 base pairs, and 5 fragments smaller than 200 base pairs.

3 Claims, 2 Drawing Sheets

HpyCH4 III Figure 1
HpyCH4 III Mapping Digests:
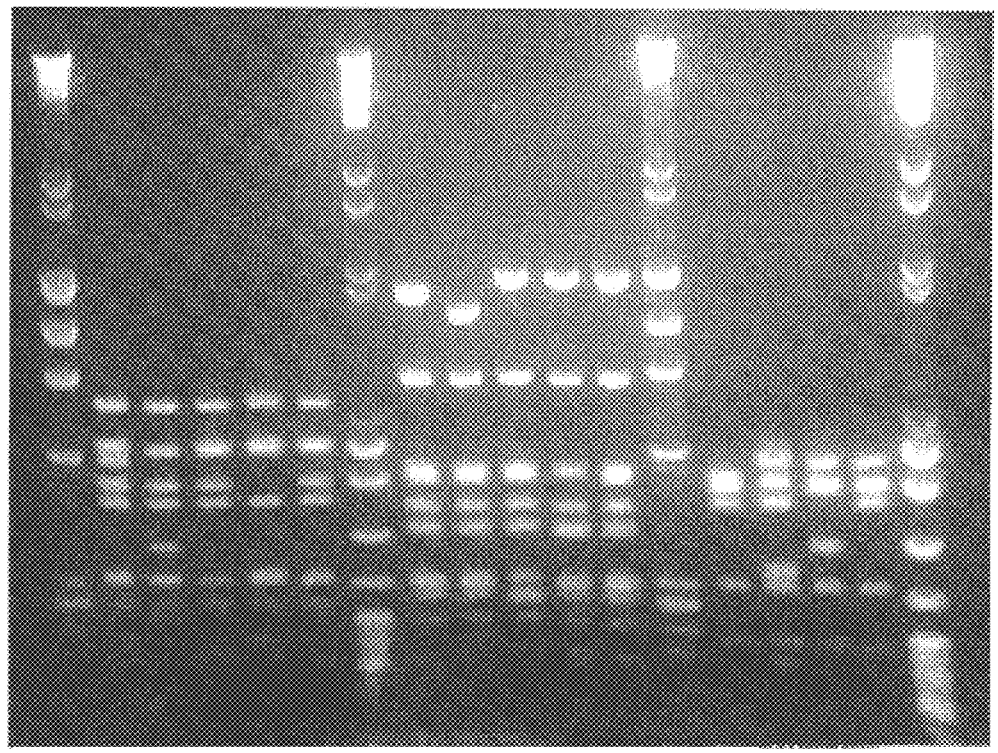

HpyCH4 III Figure 2
NEB#1233
cut A C G T cut
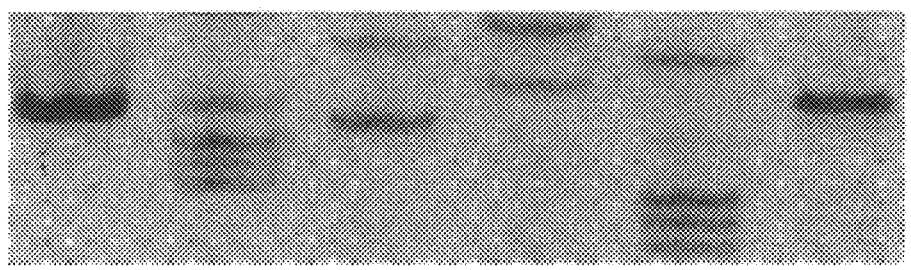
NEB#1224
cut A C G T cut
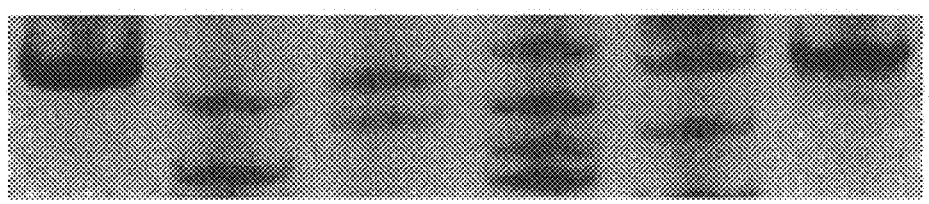

```
                         SEQUENCE LISTING

<160> NUMBER OF SEQ ID NOS: 6

<210> SEQ ID NO 1
<211> LENGTH: 6
<212> TYPE: DNA
<213> ORGANISM: Haemophilus aegyptius

<400> SEQUENCE: 1 wggccw                                                                   6

<210> SEQ ID NO 2
<211> LENGTH: 6
<212> TYPE: DNA
<213> ORGANISM: Escherichia coli

<400> SEQUENCE: 2 gaattc                                                                   6

<210> SEQ ID NO 3
<211> LENGTH: 5
<212> TYPE: DNA
<213> ORGANISM: Helicobacter pylori
<220> FEATURE:
<223> OTHER INFORMATION: "N" at position 3 represents either G, C, A or
      T.

<400> SEQUENCE: 3 acngt                                                                    5

<210> SEQ ID NO 4
<211> LENGTH: 24
<212> TYPE: DNA
<213> ORGANISM: Helicobacter pylori

<400> SEQUENCE: 4
cgccagggtt ttcccagtca cgac                                              24

<210> SEQ ID NO 5
<211> LENGTH: 24
<212> TYPE: DNA
<213> ORGANISM: Helicobacter pylori

<400> SEQUENCE: 5
agcggataac aatttcacac agga                                              24

<210> SEQ ID NO 6
<211> LENGTH: 15
<212> TYPE: PRT
```

-continued

```
<213> ORGANISM: Helicobacter pylori
<220> FEATURE:
<223> OTHER INFORMATION: "X" at position 1 and 2 is any amino acid

<400> SEQUENCE: 6

Xaa Xaa Ile Ser Glu Val Lys Thr Ala Phe Lys Ile Ala Asp Val
 1               5                  10                  15
```

TYPE II RESTRICTION ENDONUCLEASE, HPYCH4III, OBTAINABLE FROM HELICOBACTER PYLORI CH4 AND A PROCESS FOR PRODUCING THE SAME

BACKGROUND OF THE INVENTION

The present invention relates to a new Type II restriction endonuclease, HpyCH4III, obtainable from Helicobacter pylori CH4, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence, while HaeII, which recognizes 5'-(Pu)GCGC(Py)-3' typifies restriction endonucleases having a degenerate or relaxed recognition sequence. Endonucleases with symmetrical recognition sequences generally cleave symmetrically within or adjacent to the recognition site, while those that recognize assymetric sequences tend to cleave at a distance of from 1 to 18 nucleotides away from the recognition site. More than two hundred unique restriction endonucleases have been identified among several thousands of bacterial species that have been examined to date.

Endonucleases are named according to the bacteria from which they are derived. Thus, the species Haemophilus aegyptius, for example synthesizes 3 different restriction endonucleases, named HaeI, HaeII and HaeIII. These enzymes recognize and cleave the sequences 5'-(W)GGCC(W)-3' (SEQ ID NO:1), 5'-(Pu)GCGC(Py)-3' and 5'-GGCC-3' respectively. Escherichia coli RY13, on the other hand, synthesizes only one enzyme, EcoRI, which recognizes the sequence 5'-GAATTC-3' (SEQ ID NO:2).

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always modified, by virtue of the activity of its modification methylase and it is therefore insensitive to the presence of the endogenous restriction endonuclease. It is only unmodified, and therefore identifiably foreign, DNA that is sensitive to restriction endonuclease recognition and attack. More than 3000 restriction endonucleases have been isolated from various bacterial strains. Of these, more than 200 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci. U.S.A.* 80:402 (1983)).

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from Helicobacter pylori CH4 (NEB#1236), hereinafter referred to as "HpyCH4III", which endonuclease:

(1) recognizes the nucleotide sequence 5'-ACNGT-3' (SEQ ID NO:3) in a double-stranded DNA molecule as shown below,

5'-ACN↓GT-3'
3'-TG↑NCA-5'

(wherein G represents guanine, C represents cytosine, A represents adenine, T represents thymine and N represents either G, C, A, or T);

(2) cleaves said sequence in the phosphodiester bonds between the N and G as indicated with the arrows to create blunt ends; and (3) cleaves double-stranded PhiX174 DNA to produce 15 fragments, including fragments of 1284, 814, 536, 517, 454, 404, 302, 292, 270 and 222 base pairs, and 5 fragments smaller than 200 base pairs.

The present invention further relates to a process for the production of the novel restriction endonuclease HpyCH4III. This process comprises either culturing Helicobacter pylori Ch4 under conditions suitable for expressing HpyCH4III, collecting the cultured cells, obtaining a cell-free extract therefrom and separating and collecting the restriction endonuclease HpyCH4III from the cell-free extract, or culturing a transformed host, such as *E. coli*, containing the genes for the *Hpy*CH4III methylase and endonuclease, collecting the cultured cells, obtaining a cell-free extract therefrom and separating and collecting the restriction endonuclease *Hpy*CH4III from the cell-free extract.

BRIEF DESCRIPTION OF THE FIGURES

FIG. 1—Agarose gel showing HpyCH4III cleavage of various DNAs.

FIG. 2—Determination of the HpyCH4III cleavage site.

DETAILED DESCRIPTION OF THE INVENTION

The recognition sequence of the endonuclease of the present invention may be determined by mapping the locations of several *Hpy*CH4III cleavage sites in various DNAs and comparing the DNA sequences of these regions for homology, then comparing the predicted cleavage fragments of the putative recognition sequence with the observed restriction fragments produced by *Hpy*CH4III cleavage of various DNAs. The endonuclease *Hpy*CH4III was found to cleave PhiX174 DNA more than ten times, producing fragments of approximately 1300, 825, 530, 450, 400, 300, 275 and 225 bp, along with a number of smaller fragments. The location of several cut sites were mapped to approximate positions of 5300 and 1200 (the 1300 bp fragment) by simultaneously digesting PhiX174 DNA with HpyCH4III and with endonucleases which cleave at known positions, such as SspI, NciI, StuI and PstI (FIG. 1). The approximate size of several of the larger DNA fragments produced by *Hpy*CH4III digestion of PhiX174 DNA were entered into the program SITES (Gingeras, et al., *Nucl. Acids Res.* 5:4105 (1978)), which generates potential recognition sequences for the input data by comparing the fragment sizes which would result from cleavage of the DNA at any given recognition pattern with the input fragment sizes. One such potential pattern generated was 5'-ACNGT-3' (SEQ ID NO:3), which occurs in PhiX174 DNA at positions consistent with the mapping data obtained, i.e. at positions 5294 and 1192, as well as 13 other sites. The size of fragments predicted from cleavage at 5'-ACNGT-3' sites in PhiX174, pBR322, pUC19 and M13mp18 DNAs matched the observed size of fragments from cleavage of these DNAs with *Hpy*CH4III, from which we conclude that HpyCH4III recognizes the sequence 5'-ACNGT-3'.

The point of cleavage within the HpyCH4III recognition sequence may be determined through dideoxy sequencing analysis of the terminal base sequence obtained from HpyCH4III cleavage of a suitable DNA substrate (Sanger, et al., *PNAS* 74:5463–5467 (1977) Brown, et al., *J. Mol. Biol.* 140:143–148 (1980)). By the above referenced method (FIG. 2, exemplified in Example II) it was found that *Hpy*CH4III cleaves the phosphodiester bond between the unspecified nucleotide N and the G in the recognition sequence 5'-ACNGT-3' (SEQ ID NO:3) to produce a one base 3 prime extension, as indicated by the arrows:

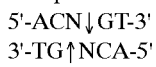

The enzyme of the present invention also has the following properties:

In accordance with the present invention, *Hpy*CH4III is obtained by culturing *Helicobacter pylori* CH4 and recovering the endonuclease from the cells. A sample of Helicobacter pylori CH4 (NEB#1236) has been deposited under the terms and conditions of the Budapest Treaty with the American Type Culture Collection (ATCC) on Sep. 23, 1999 and bears the Patent Accession No. PTA-781.

For recovering the enzyme of the present invention *Helicobacter pylori* CH4 may be grown using any suitable technique. For example, *Helicobacter pylori* CH4 may be grown in Brucella broth media (BBL Microbiology Systems, Cockeysville, Md.) incubated anaerobically at 37° C. Cells in the late logarithmic stage of growth are collected by centrifugation and either disrupted immediately or stored frozen at −70° C.

The *Hpy*CH4III enzyme can be isolated from *Helicobacter pylori* CH4 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing *Hpy*CH4III. The *Hpy*CH4III endonuclease is then purified from the cell-free extract by ion-exchange chromatography, affinity chromatography, molecular sieve chromatography, or a combination of these methods to produce the endonuclease of the present invention.

The endonuclease of the present invention along with its corresponding methylase may also be obtained using recombinant DNA techniques, such as the methylation selection technique disclosed by Wilson, et al., U.S. Pat. No. 5,200,333. As an example, DNA from a bacterial strain which contains an R-M system, such as *Helicobacter pylori*, is purified, partially digested with suitable type II endonucleases, and ligated to an appropriate cleaved, dephosphorylated cloning vector. The ligated DNA is transformed into an appropriate host, such as *E. coli*, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus be immune from cleavage. The challenged clone pools are then transformed back into the appropriate host to recover the undigested, presumably methylase expressing clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

The present invention is further illustrated by the following Examples. These Examples are provided to aid in the understanding of the invention and are not construed as a limitation thereof.

The references cited above and below are herein incorporated by reference.

EXAMPLE I

PRODUCTION OF HpyCH4III ENDONUCLEASE

*Helicobacter pylori* CH4 strain NEB#1236 was grown in Brucella broth media. The cells were incubated anaerobically under 5% $CO_2$ at 37° C. until late logarithmic stage. The cells were then harvested by centrifugation and stored frozen at −70° C. 8 grams of the cells obtained above were suspended in 40 mls buffer A (20 mM Tris-HCl, 0.1 mM EDTA, 1 mM dithiothreitol, 5% glycerol, pH 7.6 at 25° C.) adjusted to 50 mM NaCl. The cell suspension was sonicated until approximately 50 mg protein per gram of cells was released. The lysate was centrifuged at 15,000 rpm for 20 minutes at 4° C. in a Beckman JA17 rotor. 44 ml of supernatant was obtained containing 400 mg of soluble protein.

The supernatant solution was applied to a 20 ml Heparin Hyper-D column (Biosepra, Marlborough, Mass.) equilibrated in buffer A adjusted to 50 mM NaCl. A 40 ml wash of buffer A adjusted to 50 mM NaCl was applied, then a 200 ml linear gradient of NaCl from 50 mM to 1 M in buffer A was applied and fractions of 4 ml were collected. Fractions were assayed for HpyCH4III endonuclease activity by incubation with 1 µg Lambda DNA (NEB) in 50 µl NEBuffer 4 for one hour at 37° C. *Hpy*CH4III activity eluted at 0.31 M to 0.49 M NaCl.

The Heparin Hyper-D column fractions containing the *Hpy*CH4III activity were pooled, diluted to 100 mM NaCl in buffer A and applied to a 3 ml Heparin-TSK column (Toso-Haas, Philadelphia, Pa.) and a 50 ml linear gradient from 0.1 M to 0.6 M NaCl in buffer A was applied to the Heparin-TSK column. The *Hpy*CH4III activity eluted between 0.37 M to 0.43 M NaCl and contained approximately 5,000 units of endonuclease activity. The *Hpy*CH4III obtained was substantially pure and free of contaminating endonuclease and exonuclease activities. A portion of this endonuclease was used to obtain amino-terminal amino acid sequence information. To the remainder was added bovine serum albumin as a stabilizer to a final concentration of 200 µg/ml and the *Hpy*CH4III enzyme was dialyzed against storage buffer (50% glycerol, 50 mM NaCl, 20 mM Tris-HCl, 0.1 mM dithiothreitol, pH 7.5).

Activity determination

*Hpy*CH4III activity: Samples of from 1 to 10 µl were added to 50 µl of substrate solution consisting of 1X NEBuffer 4 containing 1 µg Lambda phage DNA. The reaction was incubated at 37° C. for 5 to 60 mins. The reaction was terminated by adding 15 µls of a stop solution (50% glycerol, 50 mM EDTA pH 8.0, and 0.02% Bromophenol Blue). The reaction mixture was applied to a 1.2% agarose gel and electrophoresed. The bands obtained were identified in comparison with DNA size standards.

Unit Definition: One unit of *Hpy*CH4III is defined as the amount of *Hpy*CH4III required to completely cleave 1.0 µug of Lambda DNA in a total reaction volume of 50 µl NEBuffer 4, supplemented with 100 µg/ml bovine serum albumin, within one hour at 37° C.

EXAMPLE II

Determination of the HpyCH4III Cleavage Site

The location of *Hpy*CH4III cleavage relative to the recognition sequence was determined by cleavage of a primer extension product, which was then electrophoresed alongside a set of standard dideoxy sequencing reactions produced from the same primer and template. pNEB193 DNA was employed as the template utilizing an *Hpy*CH4III recognition sites at position 453, which site was conveniently located in the vector's polylinker region downstream of priming sites for standard sequencing primers NEB#1224: 5'-dCGCCAGGGTTTTCCCAGTCACGAC-3' (SEQ ID NO:4) and NEB#1233: 5'-dAGCGGATAACAATTTCACACAGGA-3' (SEQ ID NO:5) located on either side of the polylinker.

Sequencing Reactions

The sequencing reactions were performed using the Sequenase version 2.0 DNA sequencing kit (Amersham Life Science) with modifications for the cleavage site determination. The template and primer were assembled in a 0.5 mL eppendorf tube by combining 2.5 µl dH2O, 3 µl 5×sequencing buffer (200 mM Tris pH 7.5, 250 mM NaCl, 100 mM MgCl2), 8 µl pNEB193 denatured, double-stranded DNA (4 µg) and 1.5 µl of the primer (either NEB#1224 or NEB#1233 at 3.2 µM concentration). The primer-template solutions were incubated at 65° C. for 2 minutes, then cooled to 37° C. over 20 minutes in a beaker of 65° C. water on the benchtop to anneal the primer. The labeling mix (diluted 1:20) and sequenase were diluted according to manufacturer's instructions. The annealed primer and template tube was placed on ice. To this tube were added 1.5 µl 100 mM DTT, 3 µl diluted dGTP labeling mix, 1 µl [$\alpha$-$^{33}$p] dATP (2000 Ci/mmole, 10 mCi/ml) and 3 µl diluted T7 Sequenase polymerase. The reaction was mixed and incubated at room temperature for 4 minutes. 3.5 µl of this reaction was then transferred into each of four tubes containing 2.5 µl termination mix for the A, C, G and T sequencing termination reactions. To the remaining reaction was added to 10 µl of Sequence Extending Mix, which is a mixture of dNTPs (no ddNTPs) to allow extension of the primer through and well beyond the *Hpy*CH4III site with no terminations to create a labeled strand of DNA extending through the *Hpy*CH4III recognition site for subsequent cleavage. The reactions were incubated 5 minutes at 37° C. To the A, C, G and T reactions were added 4 µl of stop solution and the samples were stored on ice. The extension reaction was then incubated at 70° C. for 20 minutes to inactivate the DNA polymerase (Sequenase), then cooled on ice. 10 µl of the extension reaction was then placed in one 0.5 ml eppendorf tube while 7 µl was placed in a second tube. To the first tube was added 1 µl (approximately 0.5 unit) *Hpy*CH4III endonuclease, the reaction was mixed, and then 2 µl was transferred to the second tube. These enzyme digest reactions were mixed and then incubated at 37° C. for 1 hour, following which 8 µl of stop solution was added and mixed. The sequencing reaction products were electrophoresed on an 6% Bis-Acrylamide sequencing gel (Novex QuickPoint system), with the *Hpy*CH4III digestions of the extension reaction next to the set of sequencing reactions produced from the same primer and template combination.

Results:

Digestion of the extension reaction product from the NEB#1224 primer with *Hpy*CH4III endonuclease produced a band which co-migrated with the unspecified nucleotide N (in this case, a T) of the *Hpy*CH4III recognition sequence 5'-ACNGT-3', indicating cleavage between the N and the G of the recognition sequence. Digestion of the extension reaction product from the NEB#1233 primer with *Hpy*CH4III endonuclease produced a band which also co-migrated with the unspecified nucleotide N (in this case the A complementary to the T of the NEB#1224 reaction sequence) of the *Hpy*CH4III recognition sequence 5'-ACNGT-3', indicating cleavage between the N and the G of the recognition sequence on this strand of DNA as well (FIG. 2). These results indicate *Hpy*CH4III cleaves DNA between the N and G in its recognition sequence on both DNA strands 5'-ACN↓GT-3', to produce a one base 3' extension.

EXAMPLE III

Determination of N-Terminal Amino Acid Sequence from the HpyCH4III Endonuclease

The *Hpy*CH4III restriction endonuclease protein is purified to near homogeneity from *Helicobacter pylori* CH4 by a combination of protein purification techniques developed at New England Biolabs (see Example I). The endonuclease so purified has an apparent molecular weight of approximately 24 kilodaltons on an SDS-PAGE gel.

The amino terminal amino acid sequence of the endonuclease is obtained using an Applied BioSystems Division, Perkin-Elmer Corporation (Foster City, Calif.) 470A Protein Sequencer (Brooks, et al., *Nucleic Acids Research*, 17:979–997 (1989). The amino acid sequence obtained was: XXISEVKTAFKIADV (SEQ ID NO:6). This amino acid sequence matches the N-terminal amino acid sequence of the gene JHP0434 in the sequenced genome of strain J99. This gene is flanked by putative methylases on both sides, JHP0433 and JHP0435. We have shown that our methylase expressing clone of the HpyCH4 IV methylase, isolated from strain CH4 (see patent application Ser. No. 09/404, 671) matches the JHP0435 methylase gene, so we believe that the HpyCH4III methylase gene will likely have strong homology to the JHP0433 putative methylase gene. We will use the amino acid sequence obtained from HpyCH4III endonuclease protein to identify the likely locus of the HpyCH4III endonuclease and methylase in the genome of strain CH4, then use the DNA sequence of the sequenced strain J99 in this region to guide PCR primer design to clone out this locus from strain CH4 in order to obtain the a clone of the endonuclease of the present invention.

What is claimed is:

1. A substantially pure Type II restriction endonuclease obtainable from *Helicobacter pylori* (ATCC Accession No. PTA-781 recognizing the following base sequence in double-stranded deoxyribonucleic acid molecules:

5'-ACN↓GT-3'

3'-TG↑NCA-5' and having a cleavage position defined by the arrows.

2. A method for obtaining the Type II restriction endonuclease of claim 1, comprising cultivating a sample of *Helicobacter pylori* under conditions favoring the production of said endonuclease and separating said endonuclease therefrom.

3. The type II restriction endonuclease of claim 1, wherein the restriction endonuclease is purified from *Helicobacter pylori* (ATCC Accession No. PTA-781).

\* \* \* \* \*

UNITED STATES PATENT AND TRADEMARK OFFICE
CERTIFICATE OF CORRECTION

PATENT NO.   : 6,238,904 B1
DATED        : May 29, 2001
INVENTOR(S)  : Richard D. Morgan and Qing Xu It is certified that error appears in the above-identified patent and that said Letters Patent is hereby corrected as shown below:

<u>Title page,</u>
In the Title, before "TYPE" insert a -- A NOVEL --

<u>Column 1,</u>
Line 43, replace "assymmetric" with -- asymmetric --
Line 64, replace "ecule" with -- ecules --

<u>Column 5,</u>
Line 6, replace "sites" with -- site --
Line 46, replace "1.0 μug'" with -- 1.0 μg --

<u>Column 6,</u>
Line 5, replace "dH2O" with -- $dH_2O$ --
Line 7, replace "MgC12" with -- $MgCl_2$ --
Line 21, delete "to" second occurrence
Line 39, replace "an" with -- a --

<u>Column 9,</u>
Line 15, replace "PTA-781" with -- PTA-781) --

<u>Column 10,</u>
Line 16, replace "type" with -- Type --

Signed and Sealed this

Fifteenth Day of January, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,238,904 B1
DATED : May 29, 2001
INVENTOR(S) : Morgan et al.

It is certified that error appears in the above-identified patent and that said Letters Patent is hereby corrected as shown below:

Column 1,
Line 6, insert
-- This invention was made with Government support under contract number DK53707 awarded by the National Institutes of Health. The Government has certain rights in the invention. --

Signed and Sealed this

Twenty-eighth Day of January, 2003

JAMES E. ROGAN
*Director of the United States Patent and Trademark Office*